(12) United States Patent
Frerichs et al.

(10) Patent No.: US 7,549,422 B2
(45) Date of Patent: Jun. 23, 2009

(54) VENTILATION MASK WITH FOREHEAD SUPPORT

(75) Inventors: Arnold Frerichs, Buxtehude (DE); Gerd Schulz, Schenefeld (DE)

(73) Assignee: Weinmann Geräte für Medizin GmbH & Co. KG, Hamburg (DE)

( * ) Notice: Subject to any disclaimer, the term of this patent is extended or adjusted under 35 U.S.C. 154(b) by 685 days.

(21) Appl. No.: 11/038,783

(22) Filed: Jan. 18, 2005

(65) Prior Publication Data

US 2005/0155603 A1 Jul. 21, 2005

(30) Foreign Application Priority Data

Jan. 19, 2004 (DE) .................. 10 2004 002 870

(51) Int. Cl.
*A62B 18/02* (2006.01)
(52) U.S. Cl. ............... 128/207.11; 128/206.21; 128/205.25; 128/206.12
(58) Field of Classification Search ......... 128/206.21, 128/206.24, 205.25, 206.12, 200.24, 201.17, 128/201.12, 200.27, 201.19, 201.24, 203.29, 128/204.18, 207.14, 207.18
See application file for complete search history.

(56) References Cited

U.S. PATENT DOCUMENTS 7,069,932 B2 * 7/2006 Eaton et al. ............ 128/206.24
2003/0034034 A1 * 2/2003 Kwok et al. ........... 128/206.21

FOREIGN PATENT DOCUMENTS

DE 101 55 152 6/2002

* cited by examiner

*Primary Examiner*—Steven O Douglas
(74) *Attorney, Agent, or Firm*—Friedrich Kueffner (57) ABSTRACT

A ventilation mask has a base, a hose connection, and at least one sealing element and is provided with a forehead support. The forehead support is arranged in such a way that it can be positioned relative to the base of the mask. A connecting device that couples the forehead support with the base of the mask is flexible. The connecting device is arranged so that it can be moved relative to a guide in such a way that the connecting device projects a predeterminable distance from the guide and can be locked in at least two different positions relative to the guide.

11 Claims, 7 Drawing Sheets

VENTILATION MASK WITH FOREHEAD SUPPORT

BACKGROUND OF THE INVENTION

1. Field of the Invention

The present invention relates to a ventilation mask, which has a base, a hose connection, and at least one sealing element and is provided with a forehead support, which is arranged in such a way that it can be positioned relative to the base of the mask.

2. Description of the Related Art

Ventilation masks of this type can be designed both as nasal masks and full-face masks. Ventilation masks of this type typically have a movable forehead support that helps achieve optimum positioning of the mask on the differently shaped faces of different patients. The forehead support is usually moved relative to the base of the mask by rotation about a transverse axis or rotation about a vertical axis.

A disadvantage with respect to rotation of the forehead support relative to both a transverse axis and a vertical axis is that movements of this type only indirectly adjust the distance between the forehead support and the base of the mask.

It is also known from DE 101 55 152 that the forehead support can be adjusted relative to the base of the mask with the use of rods. However, the use of these rods or the use of screws leads to integration problems with respect to the introduction of these components in the mask geometry.

SUMMARY OF THE INVENTION

The objective of the present invention is to construct a ventilation mask of the aforementioned type in such a way that an adjusting device for the forehead support has a high degree of functionality and at the same time can be integrated in the geometric shape of the base of the mask in a simple way.

In accordance with the invention, this objective is achieved by providing a connecting device with a flexible construction for coupling the forehead support with the base of the mask and arranging it so that it can be moved relative to a guide in such a way that the connecting device projects a predeterminable distance from the guide and can be locked in at least two different positions relative to the guide.

The movable arrangement of the connecting device in the guide in such a way that variable projection of the connecting device from the guide is realized, depending on the position in which it is locked, allows direct adjustment of the ventilation mask on the patient's face. The flexible construction of the connecting device allows integration in the rounded contour of the base of the mask.

Production of the components that are used by means of injection molding techniques is assisted by constructing the connecting device with a strap-like shape.

In another embodiment, the connecting device has a spiral configuration.

It is also possible to construct the connecting device as a link chain with a rigid end piece.

Conformation to a typical contour of a ventilation mask can be achieved by providing the guide with a curved guide track for the connecting device.

Simple mechanical realization can be achieved by providing a locking device, which has at least one projecting part and at least one recess, for locking the connecting device relative to the guide.

Ease of operation is assisted by providing the connecting device with an operating button.

A structurally simple realization with the use of bending stresses within the connecting device can be achieved if the connecting device can be locked relative to the guide by spring bracing.

Increased mechanical stability and improved guiding precision can be achieved if the connecting device has two straps that run essentially parallel to each other.

In particular, it is intended that one of the straps be provided for guiding the connecting device and the other strap for supporting the connecting device.

The possibility of direct adjustment of the forehead support on the patient's face is achieved especially if an end of the connecting device that extends out of the guide runs essentially perpendicularly to a reference plane of the base of the mask.

The opposite end of the connecting device from the forehead support can be locked in position if the connecting device has at least one locking recess adapted to a locking pin at the opposite end of the connecting device from the forehead support.

The connecting device can be locked in at least two different locking positions if the connecting device has at least two locking recesses.

The various features of novelty which characterize the invention are pointed out with particularity in the claims. annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
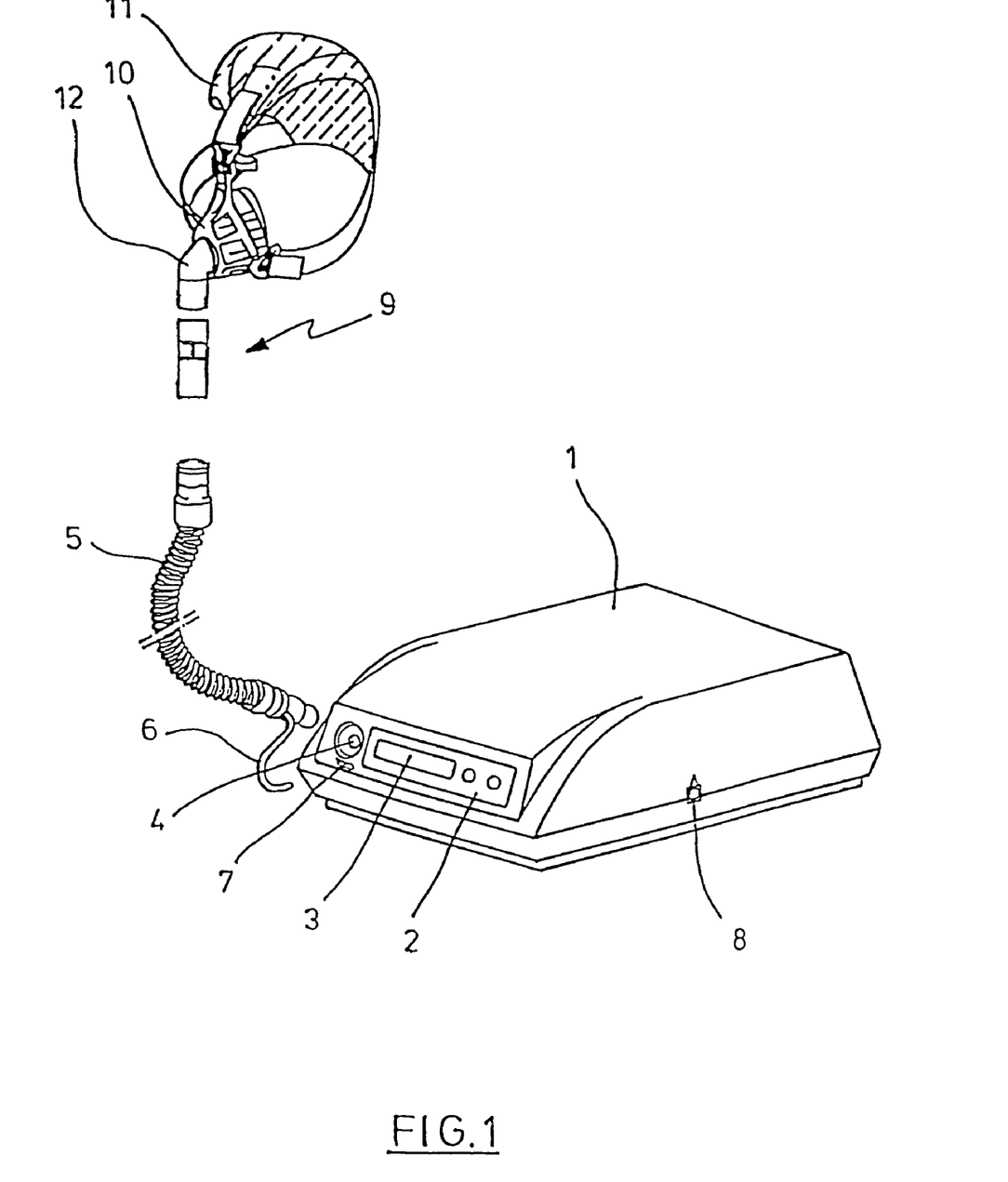
FIG. 1 is a perspective view of a ventilation device with a connecting hose running to a ventilation mask.

FIG. 1 shows the basic design of a ventilation device. In the area of the unit housing, which has an operating panel and a display, a respiratory gas pump is installed in an internal space in the unit. A respiratory gas hose is attached by a coupling. An additional pressure-measuring hose, which can be connected with the unit housing by a pressure input connection, can run along the respiratory gas hose To allow data transmission, the unit housing has an interface.

An expiratory device is installed in an expanded area of the respiratory gas hose that faces away from the unit housing An expiratory valve can also be used.

FIG. 1 also shows a ventilation mask, which is designed as a nasal mask. The mask can be fastened on the head of a patient by a head fastening device A hose coupling is provided in the expanded region of the ventilation mask that faces the respiratory gas hose.

Figure 2:
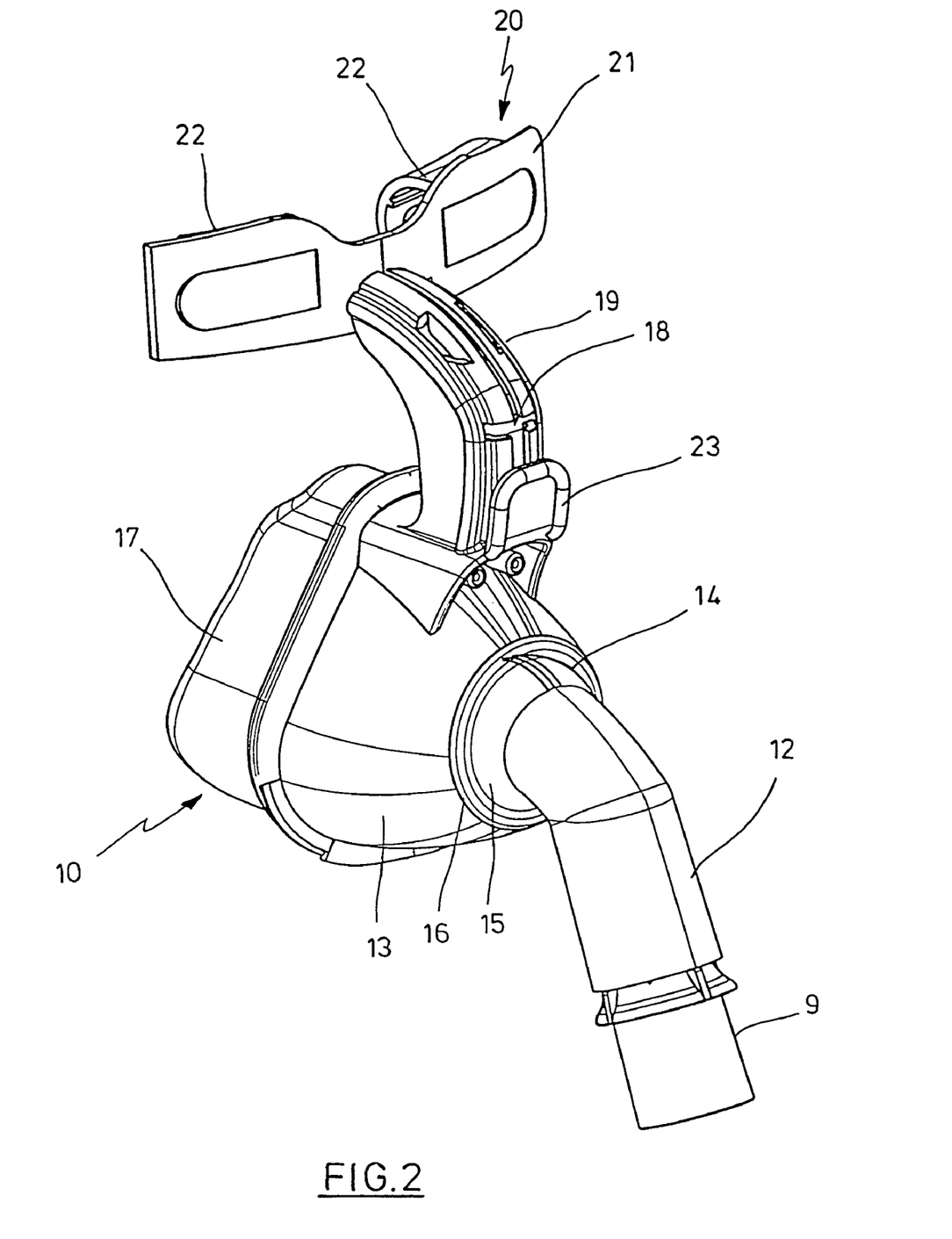
FIG. 2 is a perspective view of a ventilation mask with a forehead support, in which a connecting device between the forehead support and the base of the mask is flexible and is guided in a track.

FIG. 2 shows the design of the ventilation mask in detail. The hose coupling for the respiratory gas hose, which is not shown in this drawing, is connected with the base of the ventilation mask by a joint, which is a ball-and-socket joint. In the embodiment illustrated here, the joint consists of an inner part, which is joined with the hose coupling, and an outer shell, which is joined with the base of the mask. The inner part is designed at least regionally as a spherical segment, and the outer shell extends along at least a portion of the surface of the inner part that is shaped like a spherical segment.

A sealing element, which is designed at least regionally as a lip seal, is mounted on the base of the mask to provide a seal relative to the patient's face. A forehead support is coupled with the base of the mask by a connecting device, which is supported at least regionally by a guide The forehead support has a support that supports a forehead pad.

In the specific embodiment illustrated in FIG. 2, the guide curves away from the hose coupling starting from the base of the mask. The connecting device, which has a flexible and strap-like design, runs at least within a certain region of the guide The connecting device can be locked inside the guide in at least two different positions. An operating button is used to lock and position the connecting device. When the operating button is pressed, the lock is released, and the connecting device can be moved inside the guide After the operating button is released, the connecting device locks in place again.

Figure 3:
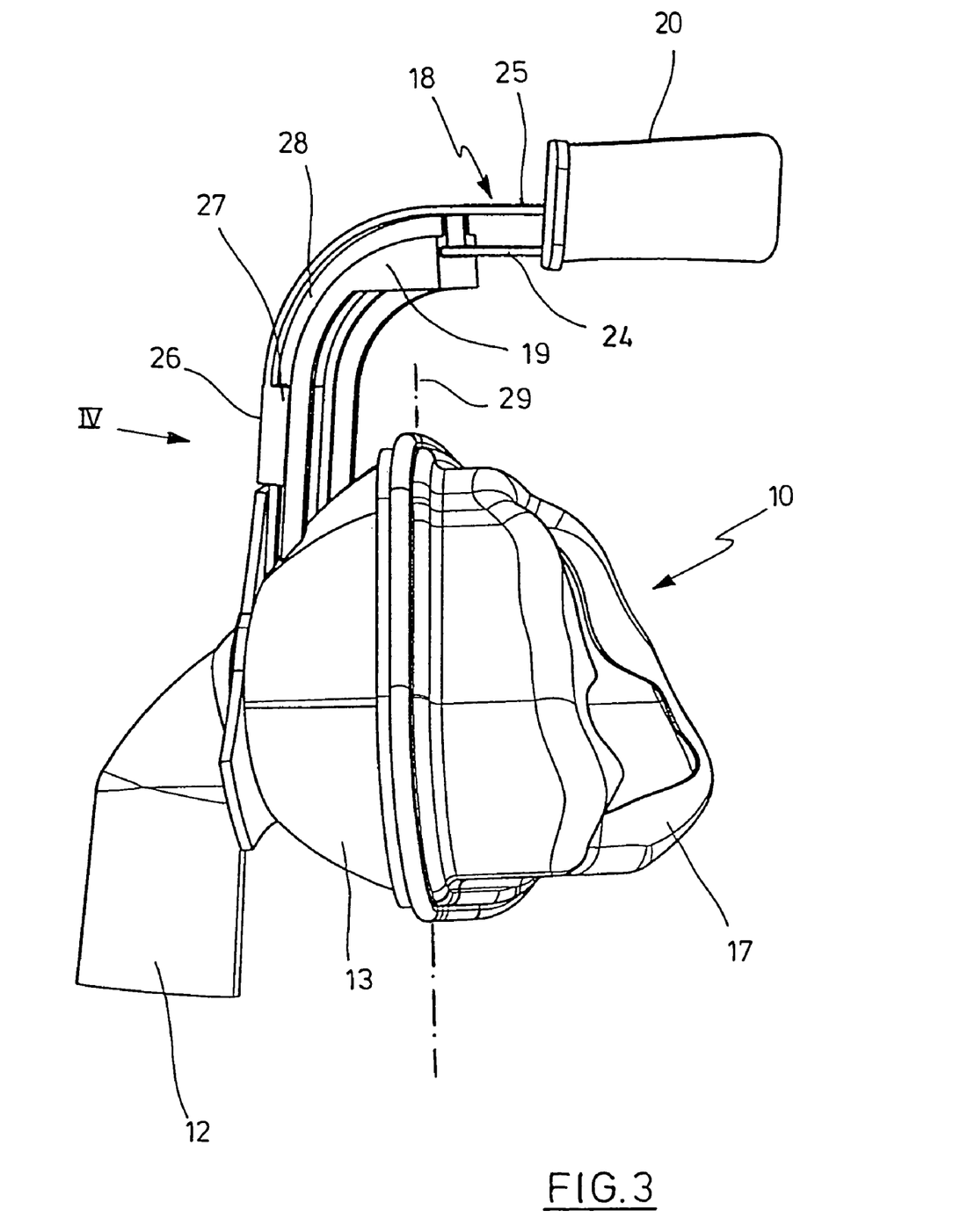
FIG. 3 is a perspective view of a different ventilation mask, in which the connecting device between the forehead support and the base of the mask comprises two flexible straps guided parallel to each other and spaced some distance apart.

In the embodiment illustrated in FIG. 3, the connecting device consists of two straps, that run essentially parallel to each other. The first strap can be positioned inside the guide while the second strap runs along an outer boundary of the guide In the region of the end piece of the strap, the strap has lateral webs, which fit into lateral grooves of the guide The end piece can be used to move the connecting device The strap serves mainly for support.

FIG. 3 illustrates that when the connecting device is moved relative to the guide, the forehead support is positioned essentially perpendicularly to a reference plane of the ventilation mask. This design supports the direct position setting of the forehead support.

Figure 4:
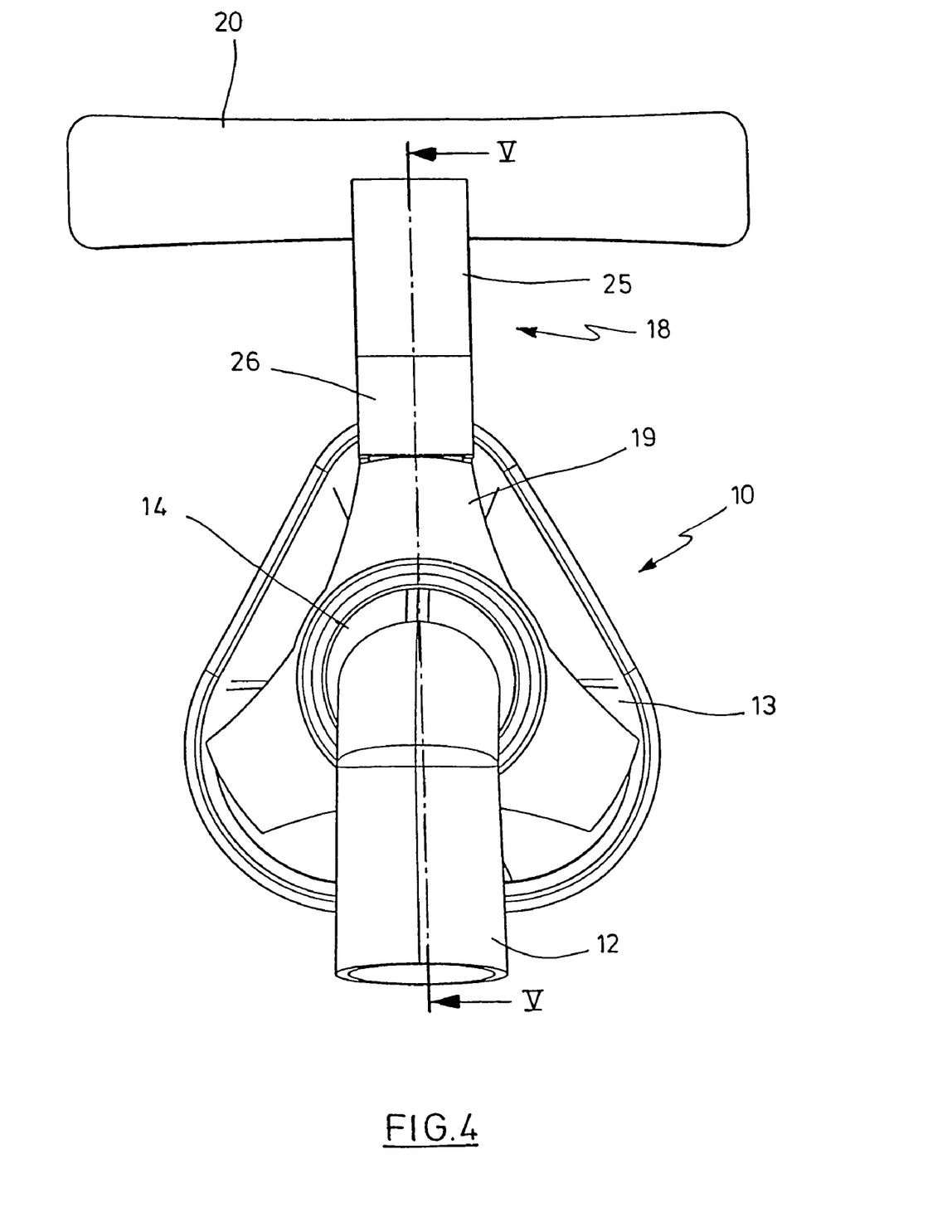
FIG. 4 is another view of the ventilation mask in FIG. 3.

FIG. 4 shows the design of the ventilation mask illustrated in FIG. 3 in viewing direction IV in FIG. 3. The essentially symmetrical construction relative to the vertical center plane in FIG. 4 is especially evident.

Figure 5:
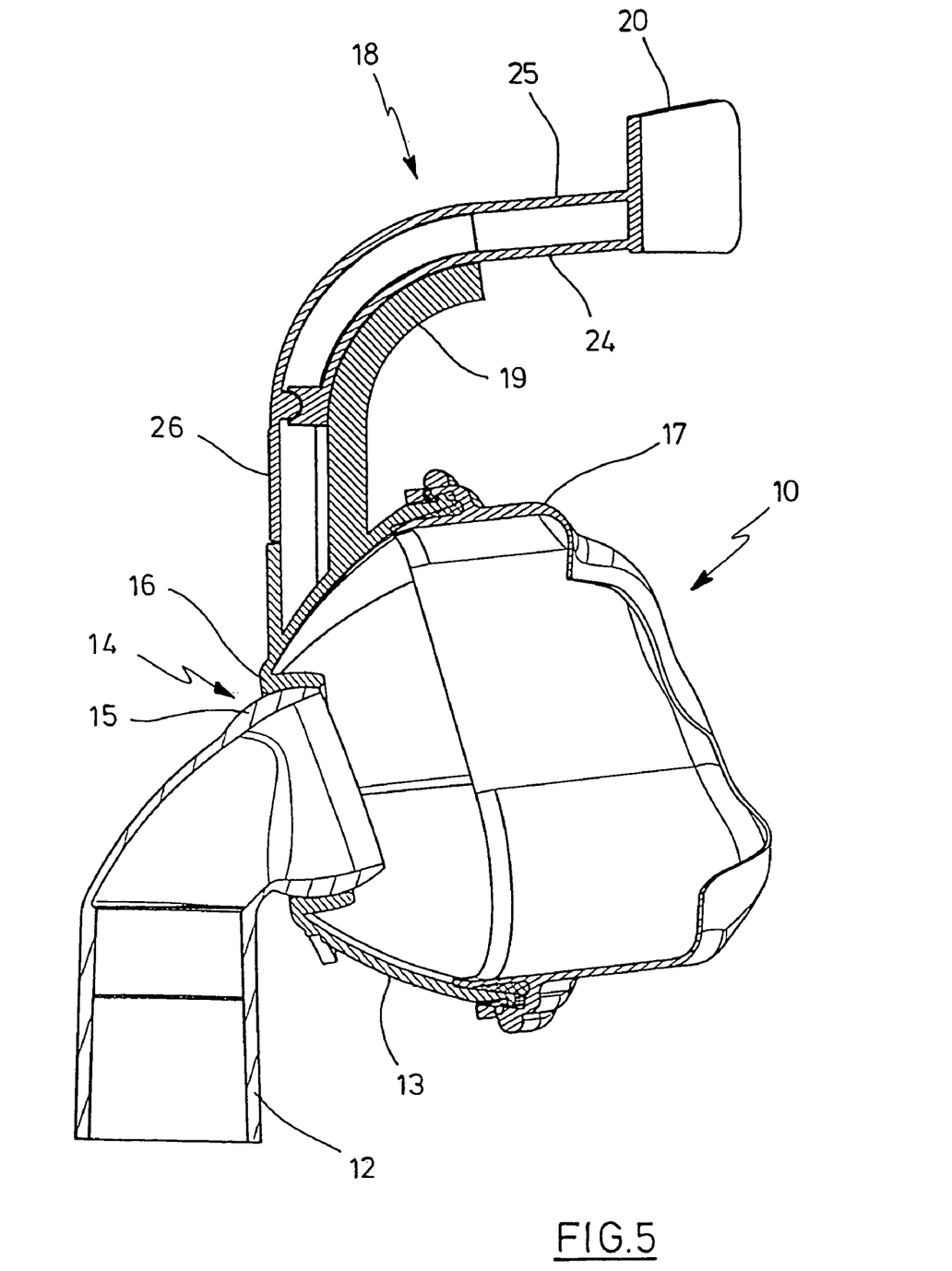
FIG. 5 is a cross sectional view along cross-sectional line V-V in FIG. 4.

FIG. 5 illustrates a vertical section through the ventilation mask in FIG. 4. The drawing reveals, for example, that the straps, are braced relative to each other inside the guide by a transverse element The transverse element comprises two parts that are formed as projections, which extend outward towards each other from the straps, and conform to each other in such a way that they fit into each other over portions thereof.

Figure 6:
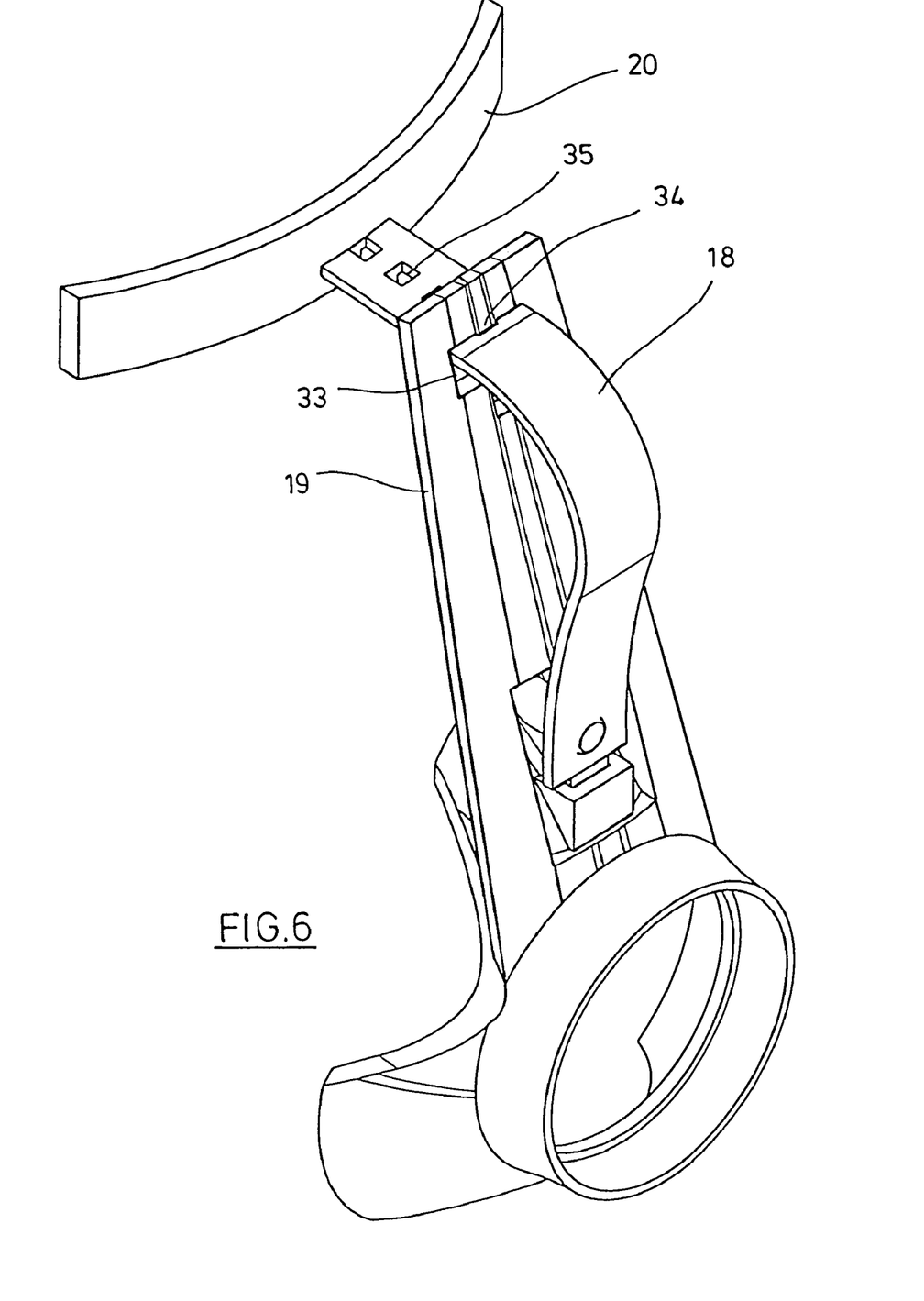
FIG. 6 shows an embodiment in which the connecting device is designed like a leaf spring and is locked in a guide.

FIG. 6 shows an embodiment in which the guide is formed separately and is designed to be joined with the base (not shown) of the mask. The connecting device is realized in the form of a strap with internal stress similar to a leaf spring. The connecting device extends through a recess of the guide. In the area of the recess, there is a projection that is formed as part of the guide When the connecting device is positioned accordingly, this projection fits into a recess of the connecting device and thus produces locking of the connecting device relative to the guide.

Several recesses are arranged in succession in the longitudinal direction of the connecting device, so that, depending on which locked position is selected, the connecting device extends a different length out of the recess, and in this way different distances of the forehead support relative to the base of the mask are realized.

In principle, it is possible to provide the embodiment shown schematically in FIG. 6 with a covering in the area of the connecting device to ensure a harmonious contour transition with the shape of the base of the mask. The connecting device is locked in the recess by the leaf-spring-like tension within the connecting device, which results from the curved shape of the connecting device, as illustrated in FIG. 6.

In the embodiment shown in FIG. 6, the connecting device has a locking recess at the opposite end from the recess. The locking recess encloses a locking pin, which is formed as part of the guide in the illustrated embodiment. To prevent unintentional separation of the connecting device and the locking pin, it is intended especially that the locking pin be provided with a thickened edge in the region that protrudes from the locking recess.

Figure 7:
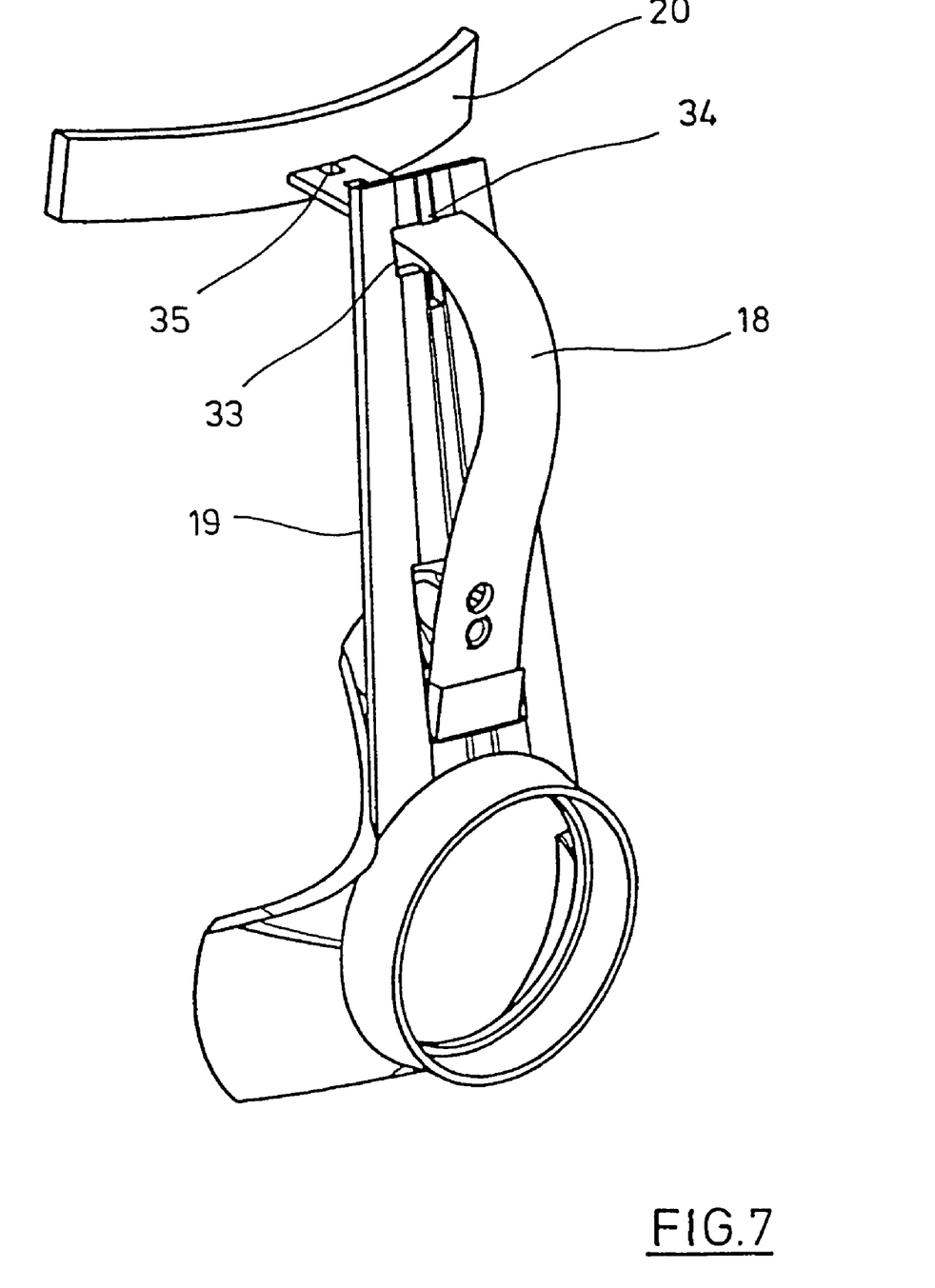
FIG. 7 shows an embodiment that is modified relative to the embodiment shown in FIG. 6 with double-adjustable locking of the connecting device.

In the embodiment shown in FIG. 7, the connecting device is provided with two locking recesses This makes it possible to preset a given locking position. As a result of this ability to preset the locking position, it is possible, depending on the length of the end of the connecting device extending from the recess in the direction of the forehead support, to preset the locking of the opposite end of the connecting device from the recess in such a way that the curvature of the connecting device between the recess and the locking recess lies within a predeterminable interval and especially that excessive deflection is avoided.

We claim:

1. A ventilation mask, comprising a base, a hose connection, at least one sealing element and a forehead support, the forehead support being arranged in such a way that it can be positioned relative to the base of the mask, further comprising a flexible connecting device that couples the forehead support with the base of the mask and is supported at least regionally by a guide, the forehead support being movably arranged relative to the guide such that the connecting device projects a predeterminable distance from the guide and can be locked in at least two different positions relative to the guide, wherein, when the connecting device is moved relative to the guide, the forehead support is positioned essentially perpendicular to a reference plane of the ventilation mask.

2. The ventilation mask in accordance with claim 1, wherein the connecting device has a strap-like shape.

3. The ventilation mask in accordance with claim 1, wherein the guide has a curved guide track for the connecting device.

4. The ventilation mask in accordance with claim 1, comprising a locking device for locking the connecting device relative to the guide, wherein the locking device has at least one projecting part and at least one recess.

5. The ventilation mask in accordance with claim 1, wherein the connecting device has an operating button.

6. The ventilation mask in accordance with claim 1, wherein the connecting device can be locked relative to the guide by spring bracing.

7. The ventilation mask in accordance with claim 1, wherein the connecting device has two straps that run essentially parallel to each other.

8. The ventilation mask in accordance with claim 7, wherein one of the straps is configured for guiding the connecting device and the other strap is configured for supporting the connecting device.

9. The ventilation mask in accordance with claim 1, wherein an end of the connecting device that extends out of the guide runs essentially perpendicularly to a reference plane of the base of the mask.

10. The ventilation mask in accordance with claim 1, wherein the connecting device has at least one locking recess adapted to a locking pin at an opposite end of the connecting device from the forehead support.

11. The ventilation mask in accordance with claim 10, wherein the connecting device has at least two locking recesses.

* * * * *